US008055054B2

(12) United States Patent
Ringermacher et al.

(10) Patent No.: US 8,055,054 B2
(45) Date of Patent: Nov. 8, 2011

(54) METHOD AND APPARATUS FOR THERMOGRAPHIC NONDESTRUCTIVE EVALUATION OF AN OBJECT

(75) Inventors: Harry Israel Ringermacher, Delanson, NY (US); Donald Robert Howard, Troy, NY (US); Bryon Edward Knight, Charlton, NY (US)

(73) Assignee: General Electric Company, Niskayuna, NY (US)

( * ) Notice: Subject to any disclaimer, the term of this patent is extended or adjusted under 35 U.S.C. 154(b) by 1362 days.

(21) Appl. No.: 11/639,724

(22) Filed: Dec. 15, 2006

(65) Prior Publication Data
US 2008/0144049 A1    Jun. 19, 2008

(51) Int. Cl.
  *G06K 9/00* (2006.01)
  *G01N 25/72* (2006.01)
  *G01N 25/00* (2006.01)
  *G01N 25/02* (2006.01)
  *G03G 5/10* (2006.01)
  *G01J 5/00* (2006.01)
  *G01J 5/02* (2006.01)
  *G01T 1/20* (2006.01)
  *G01T 1/161* (2006.01)
  *G01T 1/164* (2006.01)
  *G01K 11/30* (2006.01)
  *G01K 17/00* (2006.01)

(52) U.S. Cl. ............ 382/141; 374/5; 374/7; 374/25; 374/102; 250/316.1; 250/338.1; 250/339.11; 250/341.1; 250/341.6; 250/341.7; 250/341.8; 250/363.01; 250/363.02; 702/134; 702/135; 702/136

(58) Field of Classification Search .............. None
  See application file for complete search history.

(56) References Cited

U.S. PATENT DOCUMENTS
5,179,677 A * 1/1993 Anderson et al. ........... 392/411
(Continued)

FOREIGN PATENT DOCUMENTS
EP    0089760 A2    9/1983

OTHER PUBLICATIONS

Daniels ("Preliminary design of the portable thermal nondestructive evaluation system", PSR Report 2708, 1997, pp. 1-19).*
Santulli ("Impact damage characterisation of thermoplastic matrix composites using transmission transient thermography", Nondestructive Testing and Evaluation, vol. 19, Issue 3, 2003, pp. 79-90).*

(Continued)

*Primary Examiner* — Tom Y Lu
*Assistant Examiner* — Thomas Conway
(74) *Attorney, Agent, or Firm* — Fletcher Yoder, P.C.

(57) ABSTRACT

A non-destructive evaluation system and method is provided for detecting flaws in an object. The system includes a lamp for impinging the object with optical pulses and a focal plane array camera configured to capture the images corresponding to evolution of heat due to an impact of the optical pulses in the object. The system also includes an image acquisition system for capturing data corresponding to the images from the focal plane array camera. Both transmission mode imaging and reflection mode imaging techniques are used in an exemplary embodiment. A time of flight analysis system is also provided for analyzing the data from both transmission mode imaging technique and reflection mode imaging technique. The data from transmission mode imaging is used to determine thickness values at different points in the data and for determining location of flaws using the thickness values. The data from reflection mode imaging is used for determining depth of these flaws.

11 Claims, 5 Drawing Sheets

U.S. PATENT DOCUMENTS

| | | | |
|---|---|---|---|
| 5,711,603 A * | 1/1998 | Ringermacher et al. | 374/5 |
| 6,394,646 B1 * | 5/2002 | Ringermacher et al. | 374/7 |
| 2002/0126730 A1 | 9/2002 | Sun et al. | |
| 2002/0128797 A1 | 9/2002 | Sun | |
| 2005/0207468 A1 | 9/2005 | McCullough et al. | |

OTHER PUBLICATIONS

Maldague et al. ("A study of defect depth using neural networks in pulsed phase thermography: modeling, noise, experiments", Rev. Gen. Therm., 1998, vol. 37, pp. 704-717).*

* cited by examiner

METHOD AND APPARATUS FOR THERMOGRAPHIC NONDESTRUCTIVE EVALUATION OF AN OBJECT

BACKGROUND

The invention relates generally to a thermographic nondestructive testing technique for determining flaws in an object by determining thickness and diffusivity at different points on the surface of the object.

Over the years, various nondestructive ultrasonic measurement techniques have been utilized to determine cross-sectional thickness of cast metal and other solid objects. Conventionally, the object is probed with ultrasonic waves, which penetrate the surface and are reflected internally at the opposite side or surface of the object. Based upon the time required to receive a reflected wave, the distance to the opposite (back) side can be determined, giving the thickness of the object at that point. Unfortunately, conducting ultrasonic measurements of this sort to examine the cross-sectional thickness would usually necessitate a cumbersome and time-consuming mechanical scanning of the entire surface with a transducer. In addition, to facilitate intimate sonic contact between the transducer and the object surface, a stream of liquid couplant must be applied to the surface or, alternatively, total immersion of the object in the couplant must be accommodated. Such accommodations, however, are most often not very practical or even feasible for numerous structural and material reasons. For example, ultrasonic systems capable of scanning and analyzing geometrically complex parts are typically very expensive and complicated. In addition, a mechanical scanning of the transducer over the surface of a large object can require substantial time delays, often of several hours.

In contrast, infrared (IR) transient thermography is a somewhat more versatile nondestructive testing technique that relies upon temporal measurements of heat transference through an object to provide information concerning the structure and integrity of the object. Because heat flow through an object is substantially unaffected by the microstructure and the single-crystal orientations of the material of the object, an infrared transient thermography analysis is essentially free of the limitations this creates for ultrasonic measurements. In contrast to most ultrasonic techniques, a transient thermographic analysis approach is not significantly hampered by the size, contour or shape of the object being tested and, moreover, can be accomplished ten to one hundred times faster than most conventional ultrasonic methods if testing objects of large surface area.

Conventionally, an infrared (IR) video camera has been used to record and store successive thermal images (frames) of an object surface after heating. Each video image is composed of a fixed number of pixels. In this context, a pixel is a small picture element in an image array or frame, which corresponds to a rectangular area, called a resolution element, on the surface of the object being imaged. Because the temperature at each resolution element is directly related to the intensity of the corresponding pixel, temperature changes at each resolution element on the object surface can be analyzed in terms of changes in pixel contrast.

One known contemporary application of transient thermography is to determine the size and relative location (depth) of flaws within solid non-metal composites. Another application of transient thermography is for determining the thickness of metal objects. However, in all known contemporary techniques a calibrated reference standard for thickness is required or temperature dependent images are required to be generated which may intrinsically have greater error than required for accurate analysis.

Therefore, there is a need for a technique that can measure quantitatively, the absolute thickness, diffusivity and depth without using the thickness standards and without dependence on temperature.

BRIEF DESCRIPTION

According to one aspect of the present technique, a nondestructive evaluation system is provided for detecting flaws in an object. The system includes a lamp for impinging the object with optical pulses and a focal plane array camera configured to capture the images corresponding to evolution of heat due to impact of the optical pulses in the object. The system also includes an image acquisition system for capturing data corresponding to the images from the focal plane array camera. A time of flight analysis system is also provided for analyzing the data, and determining thickness values at different points in the data and for determining flaws using the thickness values.

According to another aspect, a method for determining thickness and depth of flaws in the object is provided. The method includes applying through-transmission mode imaging to the object and obtaining a through-transmission image of the object. The method then determines individual diffusivity values at different points in the through-transmission image. The method further includes calculating a thickness value at each respective point from the different points using a respective individual diffusivity value. The method also includes determining one or more flaws in the object based on thickness values at the plurality of points in the through-transmission image. Finally, the method includes using reflection mode imaging for determining a depth value for the one or more flaws since in through-transmission such depth measurements are not possible. Thus, combining the dual modes of thermographic imaging permits a complete characterization of a component.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The different embodiments described herein relate to nondestructive testing methods and system for determining thickness and depth of flaws in an object using high-speed IR transient thermography, particularly using the through-transmission mode and reflection mode imaging techniques.

Figure 1:
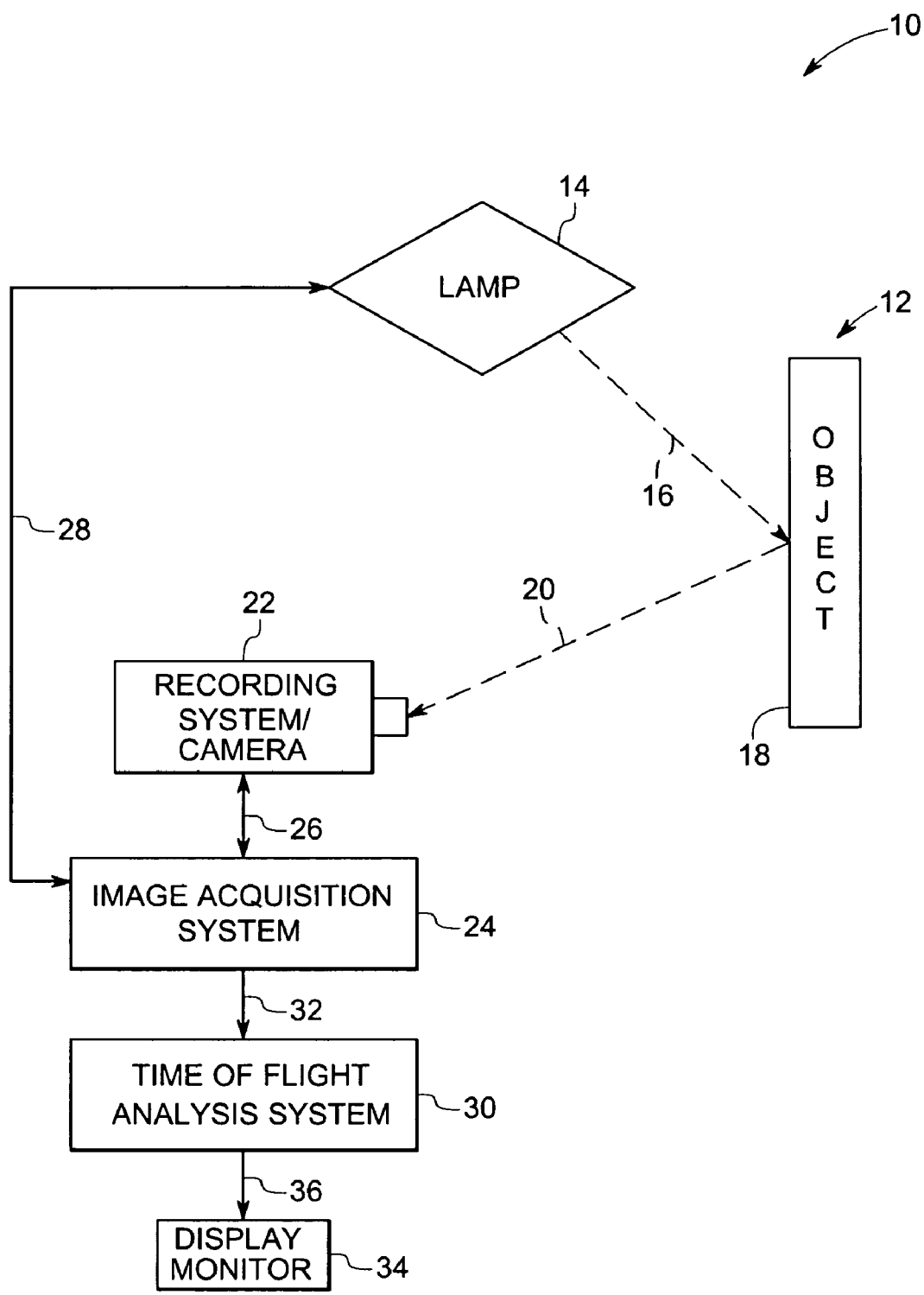
FIG. 1 is a diagrammatic representation of a non-destructive evaluation system for detecting flaws in an object.
Figure 4:
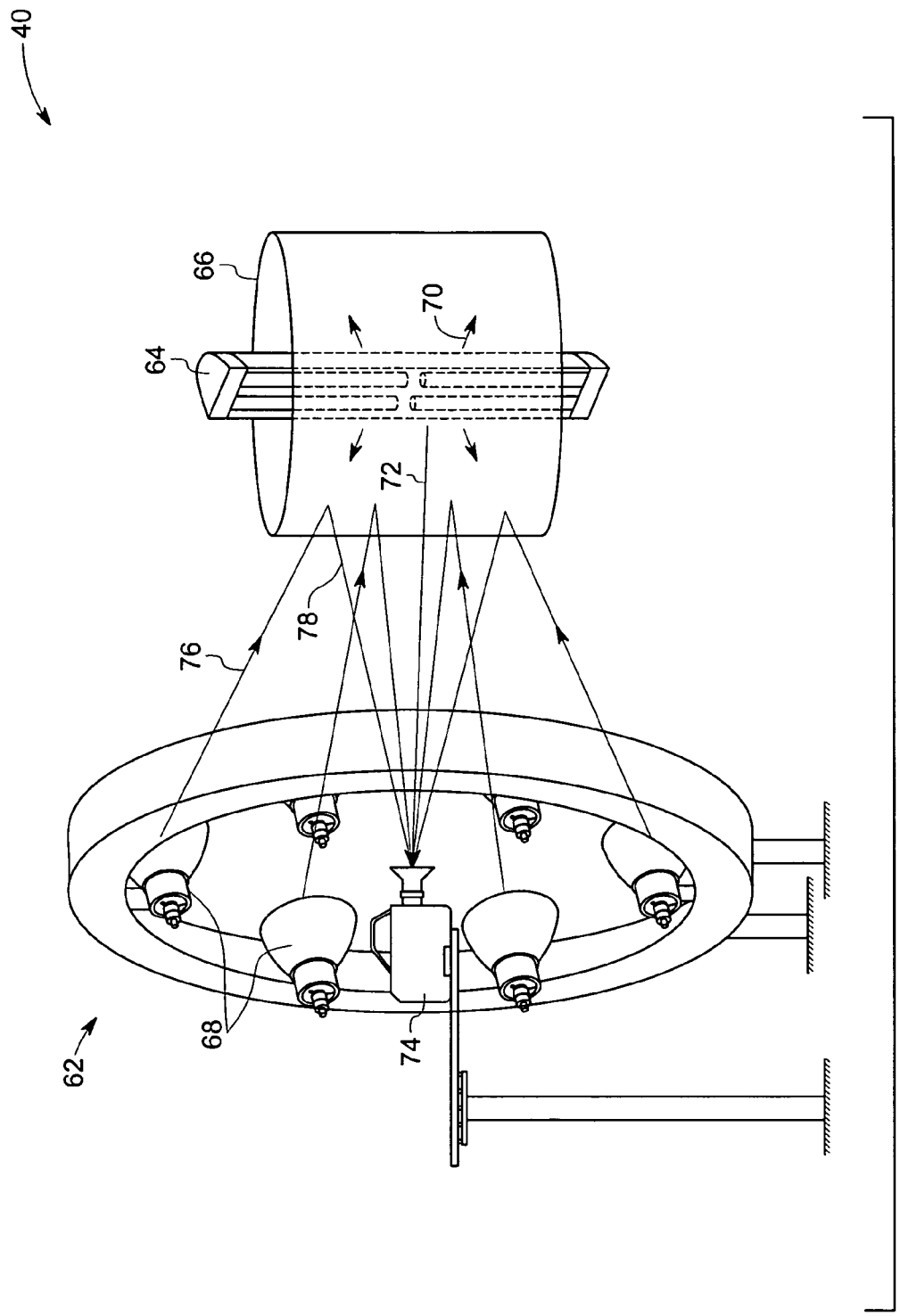
FIG. 4 is a diagrammatic representation of an exemplary embodiment with an array of lamps arranged in a circular configuration across the object and a linear lamp arrangement disposed inside the object.

FIG. 1 shows a diagrammatic representation of a non-destructive evaluation system 10 for detecting flaws in a part or an object 12. The object 12 may be an industrial part, for example, a blade (turbine blade), a vane made of ceramics, combustion liner, a shroud or a similar part, for example for turbines or aircraft components. The system 10 includes a lamp 14 (for example, a flash lamp) for rapidly applying multiple high power optical pulses 16 on a surface 18 of the object 12. In one example, the lamp 14 is a linear lamp. In an exemplary embodiment, the lamp is configured to be moved for at least one of reflection mode imaging and through-transmission imaging. Two suitable arrangements for the lamp as a heat-pulse source are shown in FIG. 4. Once an optical pulse or multiple pulses 16 are applied on the surface 18, a thermal pulse or multiple thermal pulses propagate into the object and radiate from the surface 18 back to the camera. The "reflected" waves are shown generally by reference numeral 20. Or alternately, in a specific arrangement for through-transmission imaging, the thermal pulses may be transmitted from the object 12.

The system 10 further includes a recording system or camera 22 configured to collect the reflected radiation 20 (or/and transmitted radiation) that include data representative of the propagation and evolution of the thermal pulses in the object 12. In one example, a high speed IR focal plane array camera is used as the recording system or camera 22 for monitoring and imaging the temperature or thermal profile in the object 12. It may be noted that the IR camera (e.g., a radiance HS camera available from Amber Engineering of Goleta, Calif., a Raytheon Company), in one example, captures the thermal or temperature profiles on the same side of the object 12 as the application of optical pulses by the lamp 14. In another exemplary embodiment, the focal plane array camera 22 is disposed behind the object 12 on an opposite side of the lamp 14. In the exemplary embodiment, the system 10 uses an infrared transient thermography imaging method to receive thermal images that represent the propagation of thermal pulses in the object 12 and are captured by the recording system or camera 22. The images include temperature-time responses (also referred to as T-t curves) at different points in the object 12.

The system 10 also includes an image acquisition system 24 for communicating with the recording system and camera 22 and the lamp 14 via communication links 26 and 28 respectively. In another example, the image acquisition system 24 is included within the recording system/camera 22. Acquisition of thermal data is preferably initiated at the time of firing of the lamp either by optical triggering or by other suitable means. Firing of the lamp is controlled via conventional electronics shown as the image acquisition system 24 and managed by conventional video frame acquisition software running on a system computer or a processor embodied as a time of flight analysis system 30.

The time of flight analysis system 30 is configured for capturing data represented generally by the reference numeral 32 corresponding to the images from the image acquisition system 24. The time of flight analysis system 30 is used for analyzing the data, and determining thickness values at different points in the data and for determining flaws using the thickness values. The time of flight analysis system 30 also normalizes temperature variability in the time-temperature responses while processing the time-dependence of the temperature field of the images. The time of flight analysis system 30 is further configured to use an inflection point in time of the time-temperature responses at each pixel to determine thickness and diffusivity values corresponding to different points in the object 12.

The system 10 may also include a display monitor 34 to receive an output 36 from the time of flight analysis system 30. The display monitor may be connected to a printer or any other device for displaying the output from the time of flight analysis system 30.

Figure 2:
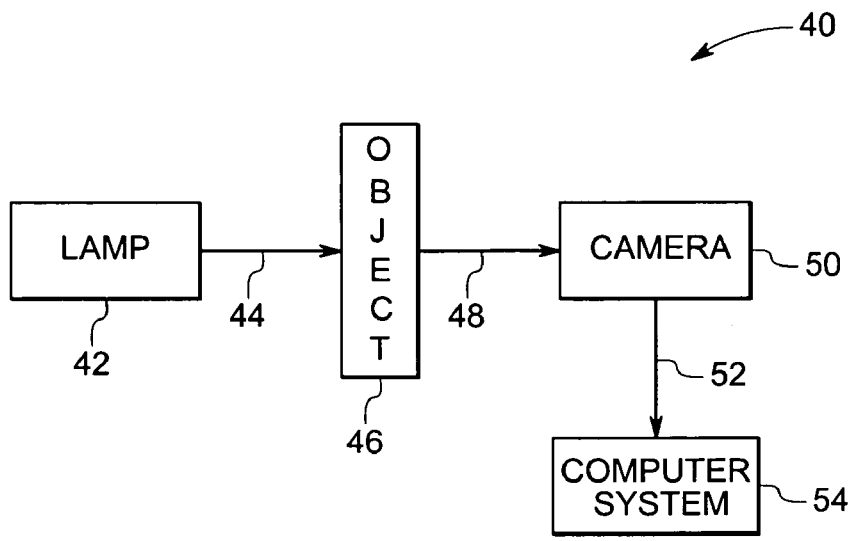
FIG. 2 is a diagrammatic representation of an exemplary embodiment with a camera positioned behind the object, on a side opposite from a lamp.
Figure 3:
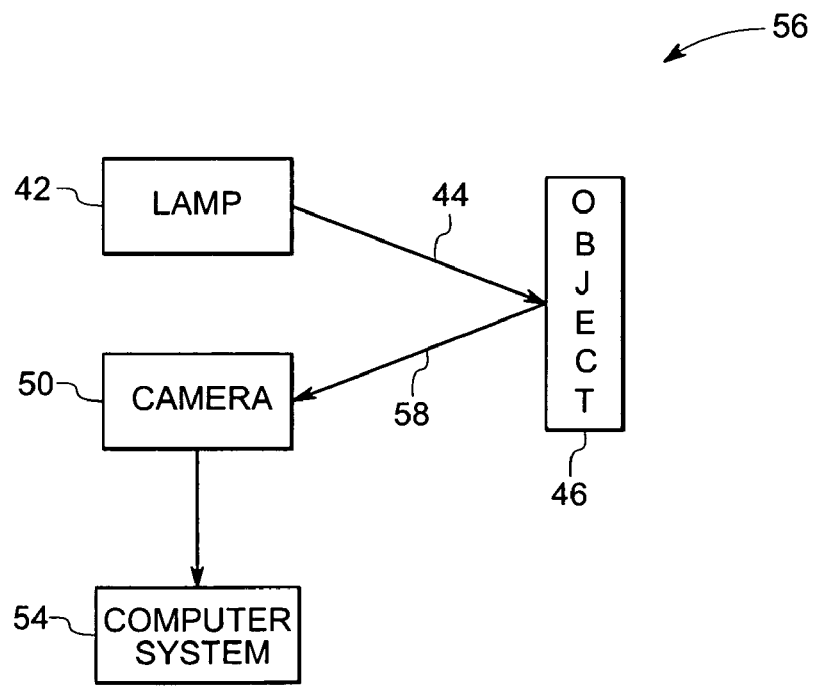
FIG. 3 is a diagrammatic representation of an exemplary embodiment with a camera on the same side as a lamp.

FIG. 2 and FIG. 3 illustrate two exemplary embodiments with different camera arrangements. FIG. 2 shows a system 40 including a lamp 42 for impinging optical-heat waves 44 on an object 46. The transmitted pulses 48, from the object 46 are captured by a camera 50 and the data 52 representing thermal images is sent to a computer system 54 for further processing. The computer system 54 may be the time of flight analysis system as described in reference to FIG. 1. The camera is positioned behind the object 46 on the opposite side of the lamp 42. This imaging technique is generally referred to as "through-transmission" mode imaging. Through-transmission imaging can detect shadows due to bubbles and delaminations, etc and gives an accurate estimate of the position of any flaws. This technique provides values for thermal diffusivity as a function of location inside the object 46 and is convenient for measuring the thickness of the flaws. Thus the output of a through-transmission imaging could be a diffusivity image or a thickness image.

FIG. 3 illustrates an alternate arrangement 56, where the camera 50 captures the reflected images 58 from the object 46. The camera 50 in this arrangement is positioned on the same side as the lamp 42 with respect to the object 46. This imaging technique is generally referred to as "reflection" mode imaging. The reflection mode imaging is advantageous for detecting discontinuities, delaminations, as a function of depth.

FIG. 4 illustrates an exemplary embodiment showing a system 40 with a lamp arrangement 62 that includes an array of lamps 68 arranged in a circular configuration across an object 66. The system 40 also includes a linear lamp arrangement 64 disposed inside the object 66. The linear lamp 64 is portable in one example. In the exemplary embodiment, first the linear lamp is used for transmission mode analysis (through-transmission imaging) of the object. The lamp 64 is placed inside the object 66 and through-transmission imaging technique is applied (arrows 70 indicate the optical pulses from the lamp 64 impinging the object 66 and arrow 72 indicates the transmitted pulses or waves from the object 66) and the through-transmission images of the object are obtained via a focal plane array camera 74. Then the reflection mode imaging is undertaken by using the lamp arrangement 62 (arrow 76 indicates the optical pulses from the array of lamps 68 and arrow 78 indicates the optical or heat pulses reflected by the object 66 and captured by the focal plane array camera 74). The object is then rotated and through-transmission imaging is again applied, followed by reflection mode imaging for the rotated object, in order to capture images from the entire object. It may be noted that the linear lamp described herein may be used independently for through-transmission imaging without the use of the circular lamp arrangement 62 and thus without the steps required for reflection mode imaging.

Figure 5:
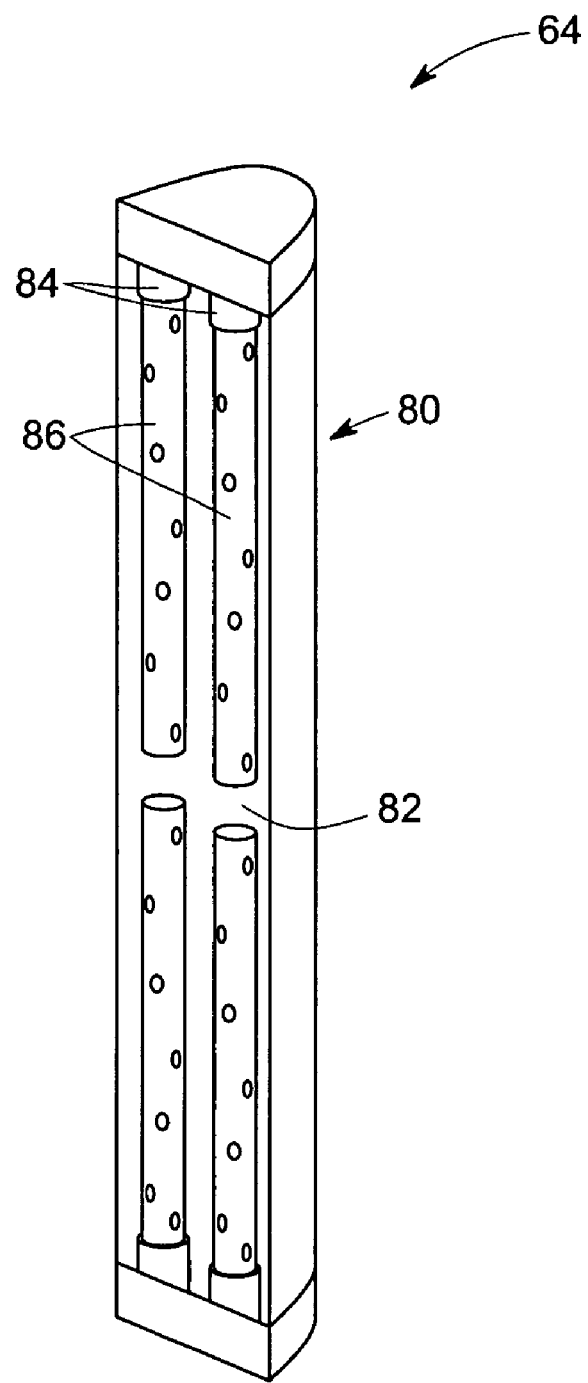
FIG. 5 is a diagrammatic representation of the linear lamp arrangement shown in FIG. 4.

One embodiment of the linear lamp 64 is shown in more detail in FIG. 5. The linear lamp 64 includes a circular reflector 80 disposed substantially around a central housing 82. The linear lamp 64 includes spaced-apart sockets 84 disposed in the central housing 82. Production bulbs 86 are configured to be held in the sockets and are placed parallel to a surface of an object being imaged. Typically, a shield (not shown) may also be used that substantially surrounds the production bulbs. The lamp is advantageously designed for high speed, broad light distribution and high power. The lamp configuration described herein allows relaible evaluation of thermal diffusivity in the object at any point of the surface of the object. In an exemplary embodiment, the linear lamp included four type MW24Q Speedotron lamps with a cylindrical reflector for optimal light distribution. The object being tested by such a lamp configuration may be of cylindrical or concave shape, in order to optimally place the linear lamp inside the object. Alternatively, the object may be hollow in another example.

Figure 6:
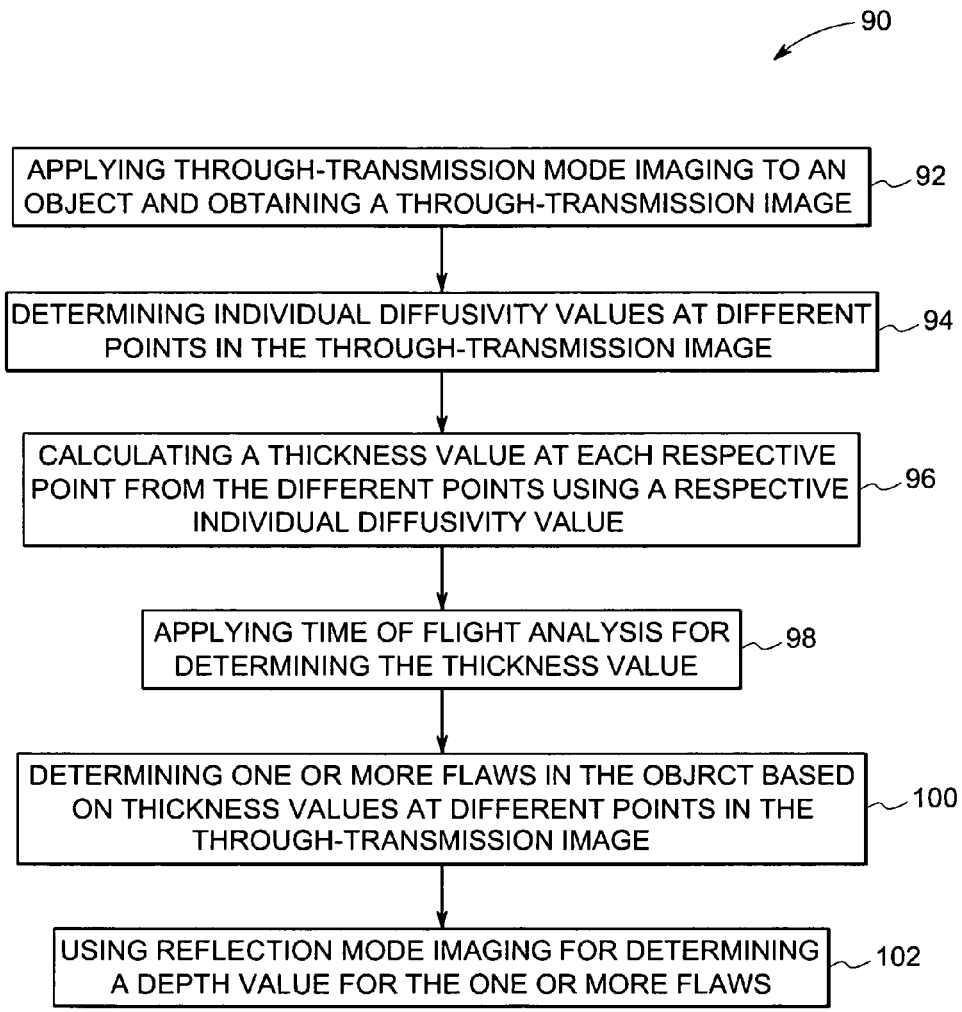
FIG. 6 is a flowchart showing exemplary steps for a method of detecting flaws in the object in accordance with aspects of the invention.

FIG. 6 illustrates a flowchart 90 showing exemplary steps for a method for determining thickness and depth of flaws in an object. The method includes a step 92 for applying through-transmission mode imaging to an object and obtaining a through-transmission image of the object. Next at step 94, the method includes determining individual diffusivity values at different points in the through-transmission image. At step 96, a thickness value is calculated at each respective point from the different points using a respective individual diffusivity value. The time of flight analysis is used at step 98, in an exemplary embodiment for determining the thickness value. Step 100 includes determining one or more flaws in the object based on thickness values at different points in the through-transmission image. It may be noted that a series of through-transmission images are taken over time in the exemplary embodiment. Finally, at step 102 reflection mode imaging is used for determining a depth value for the one or more flaws. Thus the reflection mode images are obtained in conjunction with the through-transmission images to determine values corresponding to both thickness and depth of a flaw in the object.

The time of flight analysis described herein includes using an inflection point on the T-t (temperature-time) curve obtained from the image acquisition system described in reference with FIG. 1, for analyzing the data from both transmission mode imaging technique and reflection mode imaging technique. It will be well understood by those skilled in the art, that time of flight analysis is commonly used in reference to ultrasound images, where the time of travel of sonic waves is measured. Similar concept is advantageously used in IR transient thermography, where the time of travel of thermal pulses is measured. For time of flight analysis for through-transmission imaging, the T-t curve at every pixel is examined to locate the inflection point, in time, of the curve. The time value of the inflection point is simply related to the local thermal diffusivity, given the thickness at that point. This process is simple and is accurate for homogeneous materials. It is specifically advantageous since no calibration is necessary in order to obtain the diffusivity value. The images are more robust since dependence on temperature has been eliminated. The time of flight analysis is rapid since only an inflection point is required on the T-t curve. The results, thus obtained using time of flight analysis are independent of the complex shape of a component since time of flight analysis depends on time, not temperature. Thus the thermal diffusivity calculation using time of flight analysis does not require use of any standard reference (or calibration), and therefore thermal diffusivity in the object at any point on the surface of the object can be reliably evaluated. This leads to accurate information regarding the presence, location and thickness of the flaws. The time of flight analysis for reflection mode imaging technique, similarly yields accurate information regarding depth of these flaws. Thus both thickness and depth values of the flaws can be advantageously obtained.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A non-destructive evaluation system for detecting flaws in an object; the system comprising:
   a lamp for impinging the object with optical pulses;
   a thermal camera configured to capture a plurality of images corresponding to evolution of heat due to an impact of the optical pulses in the object;
   an image acquisition system for capturing data corresponding to the plurality of images from the thermal camera; and
   a time of flight analysis system for analyzing the data to identify inflection points in a time-temperature response at a plurality of points on the object to determine thickness values at the plurality of points.

2. The system of claim 1, wherein the lamp comprises a linear lamp.

3. The system of claim 1, wherein the lamp comprises an array of lamps arranged in a circular configuration.

4. The system of claim 1, wherein the thermal camera is disposed on the same side as the lamp with respect to the object.

5. The system of claim 1, wherein the thermal camera is disposed behind the object on an opposite side of the lamp.

6. The system of claim 1, wherein the object is hollow and the lamp is disposed inside the object.

7. The system of claim 1, wherein the lamp is configured to be moved for at least one of reflection mode imaging and through-transmission imaging.

8. The system of claim 1, wherein the time of flight analysis system is used to determine flaws.

9. The system of claim 1, wherein the plurality of images comprise temperature-time responses at the plurality of points on the object.

10. The system of claim 9, wherein the time of flight analysis system normalizes temperature variability in the time-temperature responses.

11. The system of claim 10, wherein time of flight analysis system is configured to determine diffusivity values at the plurality of points.

* * * * *